United States Patent [19]
Andersson

[11] Patent Number: 6,062,861
[45] Date of Patent: *May 16, 2000

[54] METHOD AND ARRANGEMENT USING AN ARTICULATOR AND COMPUTER EQUIPMENT

[75] Inventor: Matts Andersson, Lerum, Sweden

[73] Assignee: Nobelpharma AB, Gothenburg, Sweden

[*] Notice: This patent is subject to a terminal disclaimer.

[21] Appl. No.: 09/094,400

[22] Filed: Jun. 10, 1998

Related U.S. Application Data

[63] Continuation of application No. 08/532,789, Dec. 5, 1995, Pat. No. 5,800,174.

[30] Foreign Application Priority Data

Feb. 18, 1994 [SE] Sweden .................................. 9400554

[51] Int. Cl.[7] .................................................. A61C 11/00
[52] U.S. Cl. .................................................. 433/213; 54/1
[58] Field of Search .................................. 433/213, 214, 433/215, 54

[56] References Cited

U.S. PATENT DOCUMENTS

| | | | |
|---|---|---|---|
| 4,370,130 | 1/1983 | Berger | 433/32 |
| 4,611,288 | 9/1986 | Duret et al. | 433/213 |
| 5,273,429 | 12/1993 | Rekow et al. | 433/215 |
| 5,340,309 | 8/1994 | Robertson | 433/215 |
| 5,401,170 | 3/1995 | Nonomura | 433/215 |
| 5,454,717 | 10/1995 | Andreiko et al. | 433/24 |
| 5,527,182 | 6/1996 | Willoughby | 433/172 |

FOREIGN PATENT DOCUMENTS

| | | |
|---|---|---|
| 0 490 848 | 6/1992 | European Pat. Off. . |
| 0 541 500 | 5/1993 | European Pat. Off. . |

*Primary Examiner*—John J. Wilson
*Attorney, Agent, or Firm*—Pollock, Vande Sande & Amernick

[57] ABSTRACT

An apparatus for representing position and function of the jaw and bite of an individual. The apparatus includes a computer including a memory. Information input regarding an outer surface of an object representing at least one part of the jaw and bite into the computer memory. A display for displaying vertical sections representing turning angles of the object and derived from the input information as a function of first control signals generated by the computer. A construction producer producing a construction based upon the displayed vertical sections. The construction is effected by at least one macro instruction carried out by the computer. The macro instruction codes for mathematics and rules for creating the construction. A model producer for producing a model based upon the construction. An articulator receives the model and exposes and simulates function of the outer surface of the object representing the jaw and bite of the individual.

21 Claims, 3 Drawing Sheets

METHOD AND ARRANGEMENT USING AN ARTICULATOR AND COMPUTER EQUIPMENT

This application is a continuation of Ser. No. 08/532,789 filed Dec. 5, 1995 now U.S. Pat. No. 5,800,174.

TECHNICAL FIELD

The present invention relates to a method in which an articulator is used. The jaw position/bite of an individual, and the function of this jaw position/bite, can be represented in the said articulator. The method also makes use of computer equipment, for example a personal computer, in which information concerning the jaw position/bite, or one or more parts thereof, is input into memory elements by means of a reading function. First controls can be initiated on the computer equipment, and contours or vertical sections is representative of the input information, i.e. of the jaw position/bite, or of the part(s), can be reproduced graphically on the computer screen of the computer equipment as a function of the said first controls. In addition, simulation of alterations (additions, removals, etc.) in the vertical sections or the contours can be effected with the aid of second controls on the computer equipment (its terminal, for example) in order to obtain a construction or construction alteration in the jaw position/bite or the part(s). The invention also relates to an arrangement for carrying out the said method.

PRIOR ART

The present invention makes use of, among other things, the teaching in Swedish patent application 93.02399-2. The patent in question proposes a method and arrangement for initiating, by means of a CADD program in the computer equipment, graphic representations of vertical sections or contours of an imaged object for actual use in the human body. The object can in this case be rotated about a central axis, and the object is reproduced through its different contours at different angles of rotation in a horizontal plane through the object. Alterations, for example additions, removals, etc., can be initiated on the respective contour, and in this way there is, on the whole, generous construction freedom despite the fact that there is a relatively very small quantity of available data concerning the three-dimensional structure of the object. The reading function itself also contributes to the said small quantities of data by utilizing coordinate systems in which two parameters can be varied in a predetermined manner, and only one parameter cannot be varied in a predetermined manner. The technique as such, with its associated computer equipment, is easily accessible to people who are practicing in, among other areas, the dental sector.

DESCRIPTION OF THE INVENTION

Technical Problem

In connection with the production of support members and accessories for teeth, bridges, etc., there is a requirement to achieve the necessary accuracy of manufacture using relatively small quantities of data which are intended to reproduce complicated shapes of the bodies and of the object, and alterations to such bodies and objects, the aim in this respect being for accuracies of manufacture of 0.01–0.02 mm, or greater accuracy. The invention proposes a solution to this problem, among others.

In the said production, it is important to be able to retain, to the greatest possible extent, the use of tried and tested components which are known per se, for example articulators of known type. The invention solves this problem too.

Producing a model of the object, and the routines involved in the production of constructions, alterations and additions to an individual's dentition must, in accordance with present-day requirements, be made easier for the patients, so that, for example, it is possible to carry out a smaller number of trials. This invention solves this problem too.

Notwithstanding the need for production procedures and arrangements which are simplified from the patient's point of view, it is important to provide for rational and efficient handling by the personnel carrying out the treatment, both from the technical and economic point of view. The invention provides a solution to this problem.

In accordance with the concept behind the invention, computer equipment will be used and made easily accessible to the practicing personnel. The invention solves this problem too and proposes the use of a simplified and easily manageable technique for identification, on the computer screen, of the objects which are concerned and which are of complicated shape. Integration and cooperation is possible with articulator equipment known per se.

Solution

The feature which can principally be regarded as characterizing a method according to the invention is that a model including the construction or the construction alteration is produced and is applied in the articulator. A further characteristic is that the latter is made to effect articulation movements, at the same time as the function or functions of the construction or of the construction alteration is/are exposed for observation of the function or the functions in question.

The feature which can principally be regarded as characterizing an arrangement according to the invention is that the articulator is arranged to receive a model of the jaw position/bite, including the construction or the construction alteration, and to effect articulation movements, where the function or functions of the construction or of the construction alteration can be exposed for observation of the respective function.

In one embodiment of the inventive concept, the construction or the construction alteration is a telescopic structure, a so-called cone construction, which can comprise a loose fixture consisting of a number of removable parts which are fitted on one or more support members, implants or tooth remnants, or to this/these anchored member/members. The cone construction is in this case kept in place, for example by frictional force, against the implant, the tooth remnant or the secured member.

In a further embodiment, the construction or the construction alteration consists of the application of one or more occlusion rims. The construction or the construction alteration can also relate to the relative positions between one or more teeth, tooth replacements, or support members for such teeth or tooth replacements.

In one embodiment, the construction or the construction alteration can be effected by means of one or more macro models which are used in the computer equipment. The models are initiated by means of the macro instruction which indicates mathematics and rules for creating the construction or the construction alteration, or parts thereof.

In one embodiment, the reading function is effected by means of a so-called stereophotography camera of the high-resolution type which takes a picture of the jaw position/bite, or the part(s), from photographs, model, tooth remnant, etc.

Advantages

By means of what has been proposed above, easily operated equipment is obtained which affords advantages both for patients and for the dentist/technician. An articulator which is known per se can be used, and the jaw movements, for example mastication movements, are simulated in this articulator. The newly produced constructions or construction alterations can in this way be tested with respect to their function in their environment in the jaw position or the bite. The function or the functions can be exposed to the observer in a known manner, and the observer can reapply his or her observation to further constructions or construction alterations, etc. The accuracy can be made extremely high by means of what is proposed, and the invention can be used for producing fixed and loose tooth replacements.

DESCRIPTION OF THE FIGURES

A presently proposed embodiment of a method and an arrangement according to the invention will be described below with reference to the attached drawings, in which.

DETAILED DESCRIPTION

Figure 1:
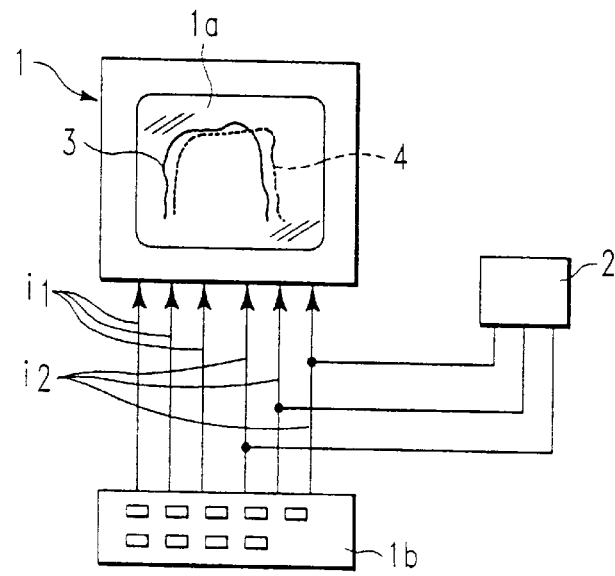
FIG. 1 shows computer equipment in the form of a personal computer.

In FIG. 1, reference 1 indicates a personal computer with a computer screen 1a. The computer equipment comprises a terminal 1b, and memory elements utilized in the computer equipment are symbolized by 2. The computer equipment is arranged to reproduce vertical sections or contours graphically on the screen, as a function of first controls $i_1$, with a first vertical section or contour, being shown by 3, and a second vertical section being shown by a broken line 4. In the present case, the vertical section 4 illustrates an addition and/or alteration to the vertical section 3, which addition and/or alteration is initiated by second signals $i_2$. As regards the more detailed structure and function of the computer, reference is made to the Swedish patent application cited.

Figure 1A:
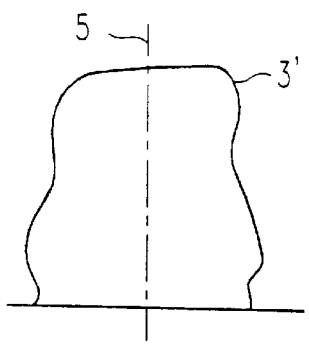
FIG. 1a shows a first contour or vertical section of a graphic reproduction on the computer equipment according to FIG. 1.
Figure 1B:
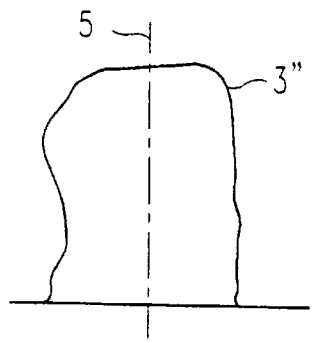
FIG. 1b shows, in vertical section, a second graphic reproduction on the computer equipment according to FIG. 1.

The said vertical sections or contours represent the vertical section or the contour of the respective imaged object. In accordance with FIGS. 1a and 1b, one vertical section at a time is reproduced on the computer screen 1a. A first vertical section of an object is symbolized by 3' in FIG. 1a. A second vertical section of the same object is indicated by 3" in FIG. 1b. The different vertical sections are taken at different angles of rotation about the center axis 5 of the object. The computer equipment can indicate, for example, 36 different vertical sections of the same object, in which case the vertical sections are taken after every tenth degree along the rotational turn of the object.

Figure 2:
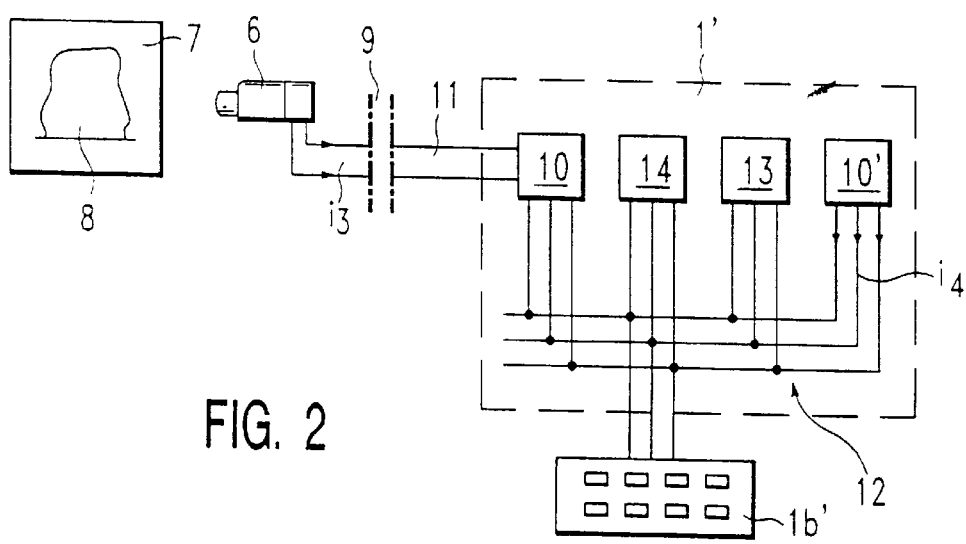
FIG. 2 shows, in block diagram form, scanning functions for the scanned object, and parts of the equipment according to FIG. 1.

According to FIG. 2, an object is scanned or read by means of a device 6 which can consist of a camera, laser scan, needle scan, etc. In the present case, the object can be imaged on a photograph, drawing or the like. The object is indicated by 8 in FIG. 2. Scanning information representing the said object is shown by $i_3$ and is transmitted on diskette, via the telephone network 9, or another medium, to the computer equipment 1'. The latter includes receiving and adapting elements 10 for receiving the information $i_3$ via a connection 11. The computer equipment includes, in a known manner, a bus connection 12. The CPU of the computer equipment is indicated by 13, and its memory elements by 14. The terminal unit 1b' is linked to the bus connection 12 in a manner known per se. The information $i_3$ representing the object 8 is thus input to the computer 1', which operates with programs by means of which the graphic reproduction, in accordance with the above, can be effected by acting on the terminal i".

Figure 3:
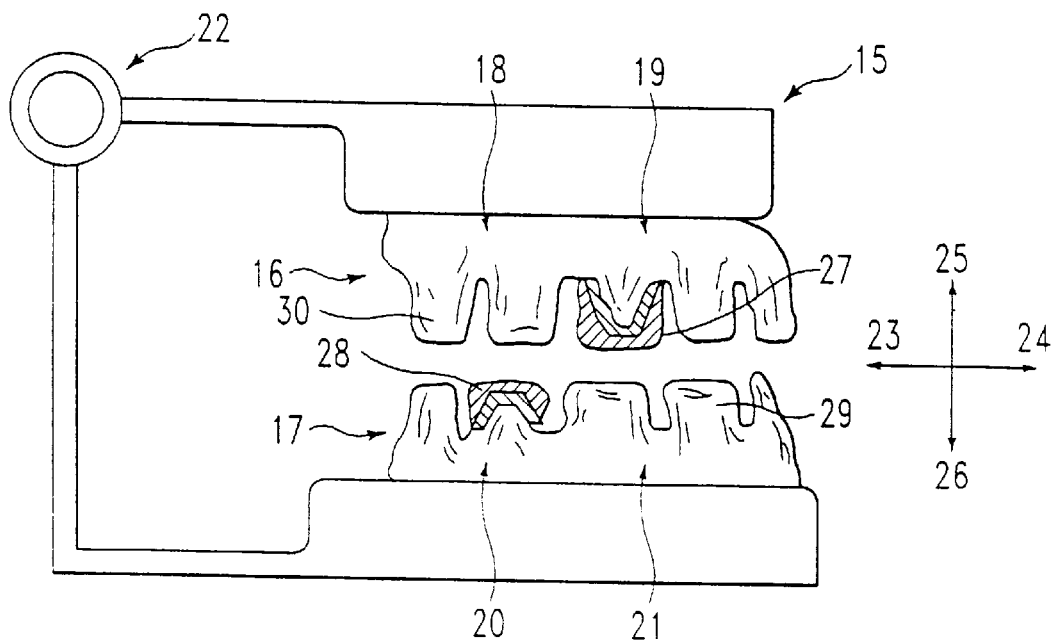
FIG. 3 shows, from the side, the principal structural parts of an articulator.

FIG. 3 shows an articulator device 15 which is known per se, and in which a jaw position 16, 17, comprising an upper jaw 16 and a lower jaw 17, is applied by means of retention elements 18, 19 and 20, 21, respectively. Jaw movements can be simulated by means of the articulator. The articulator comprises hinge member(s) 22, by means of which member(s) simulation movements can be initiated in a known manner, for example manually, electrically, pneumatically, etc. The upper and lower jaws can thus be made to execute mutually related movements for the purpose of imitating mastication movements, for example. The said movements are shown by arrows 23, 24 and 25, 26, respectively. In the jaw position according to FIG. 3, constructions or construction alterations 27, 28 have been introduced. By means of the mobility of the articulator, the respective function of the respective construction or construction alteration can be exposed and can be observed by the dental technician. By means of the articulator, the technician can picture whether the construction or the construction alteration satisfies the dental requirements, and, if this is not the case, can take the necessary measures. The constructions will be able to function with other units (teeth, bridges, implants, etc.) in the jaw position or the bite. In FIG. 3, two teeth have been indicated by 29, 30.

Figure 4:
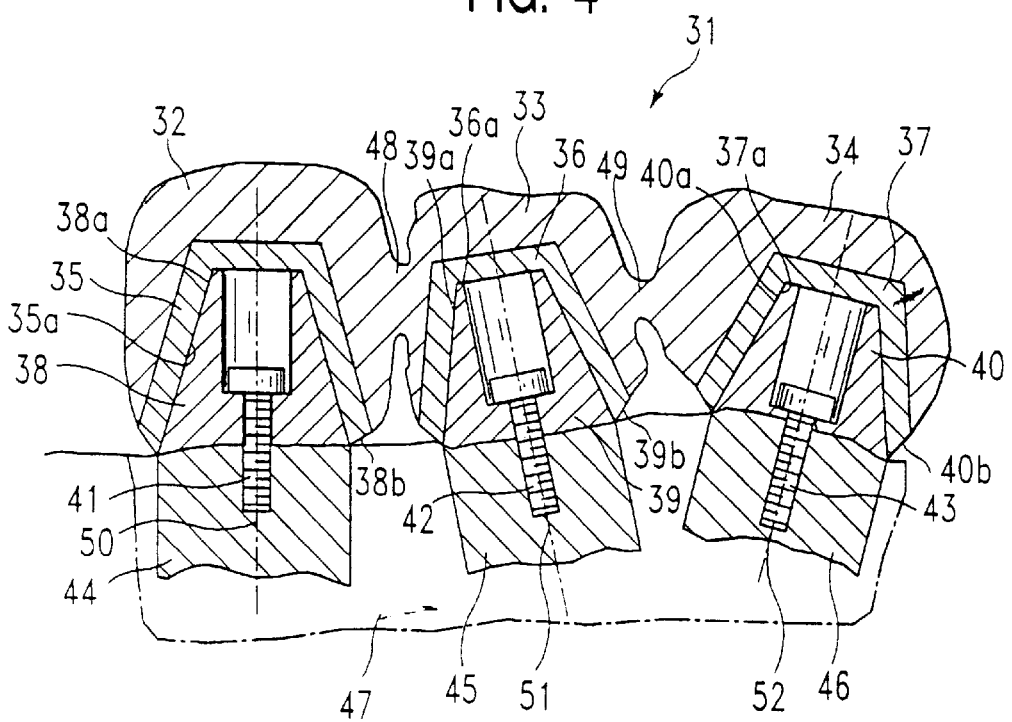
FIG. 4 shows a cone construction on implants in a jaw.

FIG. 4 shows a cone construction 31 which can be produced using the novel arrangement and method. The cone construction comprises a telescope construction or a loose fixture consisting of three tooth replacement parts 32, 33 and 34. The tooth replacement parts are built on top of caps 35, 36 and 37. The caps can be pressed, via inner surfaces 35a, 36a and 37a, on to implant parts 38, 39 and 40. The implant parts can be secured in implants 44, 45 and 46 in the jaw bone 47 by means of screws 41, 42 and 43. The said parts 38, 44 and 39, 45 and 40, 46 can alternatively consist of treated tooth remnants, or other support members which are known per se. It should be noted here that there must be great accuracy of manufacture between the outer surfaces 38a, 39a and 40a, of the parts 38, 39 and 40, and the said inner surfaces 35a, 36a and 37a. The cone construction is held together by frictional forces between the caps 35, 36 and 37 and the parts 38, 39 and 40. The junctions (angles) 38b, 39b and 40b must also be formed with great precision in order to give a well-functioning cone construction. In the present case, the tooth replacement parts 32, 33 and 34 are joined together via parts 48, 49. As is shown in FIG. 4, the center axes 50, 51 and 52, respectively, of the respective arrangement can be vertical or can be inclined in one or other direction. It is necessary, in this respect, to be able to establish great precision in the construction, so that it can be held together by means of frictional forces in all cases.

Figure 5:
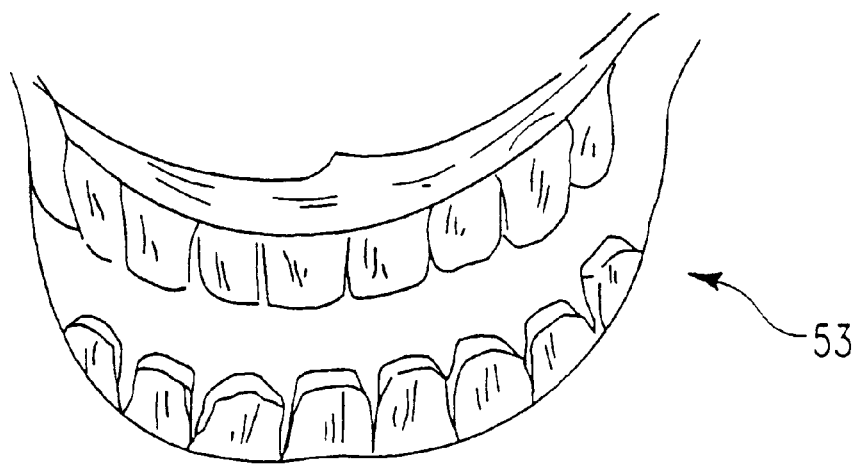
FIG. 5 shows, in perspective, a jaw position or a bite.

Thus, in accordance with the novel method, information $i_3$ will be extracted and will be received in the computer equipment 1'. The dentist or the dental technician will in this way be able to simulate the different shapes of, and additions to, the construction or the construction alteration. In FIG. 1, a specific construction is symbolized by its actual vertical section 3. The vertical section 4 is intended to show an alteration or addition which has been effected by the operator. It will be possible for output signals $i_4$, which represent the new construction, or the construction alteration which has been made, to be extracted from the computer equipment for the purpose of producing a model 53 according to FIG. 5. The model represents a jaw position or a bite which can be represented and simulated per se on the computer screen 1a. The model produced is applied in the articulator according to FIG. 3 (can also be simulated on the computer screen 1a in whole or in part). The articulator is then acted on, in accordance with the above, to simulate the said movements in the tooth position or the bite.

Figure 6:
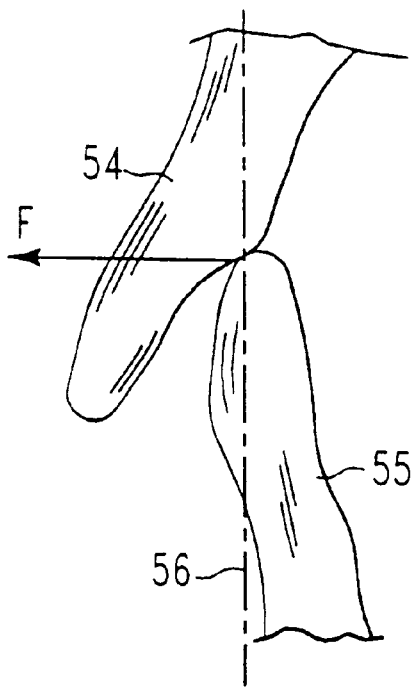
FIG. 6 shows, in vertical section, two interacting teeth in a jaw.
Figure 7:
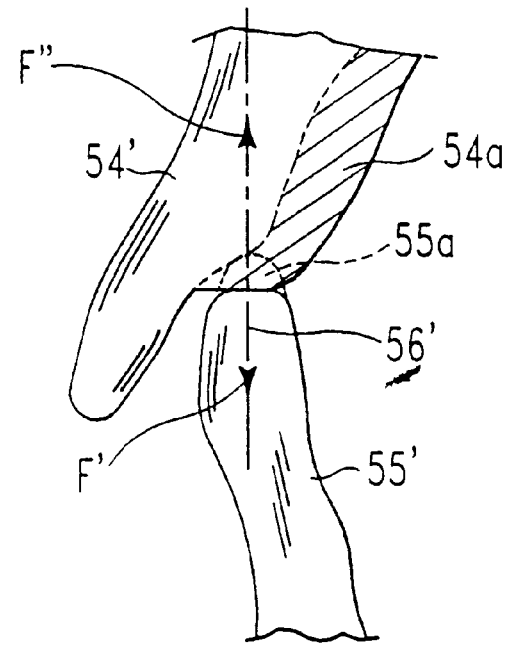
FIG. 7 shows, in vertical section, an addition to, and adjustment of, the teeth according to FIG. 6.

In FIG. 6, a tooth in the upper jaw has been symbolized by 54, and a tooth in the lower jaw has been symbolized by 55. It can be seen from the Figure that the interaction between the teeth is imposing tearing-out forces F on the upper tooth, in a direction which is at right angles to the main vertical direction 56 of the teeth. This interaction is unsatisfactory and should be corrected. FIG. 7 shows an example of how such a correction according to the invention can be carried out. The tooth 54' in the upper jaw has been provided with an added part 54a, via which the tooth 54' can interact with the tooth 55' in the lower jaw such that the forces of interaction F', F" in the upper and lower teeth essentially coincide with the essentially vertical common axis 56'. Besides the added part 54a, the lower tooth has been corrected by means of a portion 55a having been removed. The teeth according to FIGS. 6 and 7 can also be represented on the computer screen 1a. Likewise, alterations to the tooth constructions can be made with great precision in the computer equipment.

The said constructions and construction alterations can be effected in the computer equipment by means of so-called macro models and macro instructions.

The invention is not limited to the embodiment described above, but can instead be modified within the scope of the attached patent claims and the inventive concept.

I claim:

1. An apparatus for representing position and function of the jaw and bite of an individual, comprising:
   a computer including a memory;
   means for inputting information regarding an outer surface of an object representing at least one part of the jaw and bite into the computer memory;
   a display for displaying vertical sections representing turning angles of the object and derived from the input information as a function of first control signals generated by said computer;
   means for producing a construction based upon said displayed vertical sections, said construction being effected by at least one macro instruction carried out by the computer, said macro instruction coding for mathematics and rules for creating the construction;
   means for producing a model based upon the construction; and
   an articulator for receiving the model and exposing and simulating function of the outer surface of the object representing the jaw and bite of the individual.

2. The apparatus according to claim 1, wherein the information about the jaw and bite includes information about the shape of teeth, parts of teeth, teeth replacements, or support members for teeth replacements.

3. The apparatus according to claim 1, further comprising:
   means for simulating on said display alterations of the outer surfaces of the vertical sections through second control signals generated by the computer;
   means for producing on said display a construction alteration including the altered outer surfaces of the vertical sections; and
   means for producing a model based upon the construction alteration.

4. The apparatus according to claim 1, wherein the information is sensed from a tooth, part of a tooth, tooth replacement, support member for a tooth replacement, or model or photograph thereof.

5. The apparatus according to claim 1, further comprising:
   means detecting errors in the position and function of the jaw and bite after applying the model to an articulator to expose and simulate position and function of the jaw and bite of the individual;
   means for simulating on said display alterations of the outer surfaces of the vertical sections with second controls of the computer;
   means for producing a construction alteration including the displayed altered outer surface of the vertical sections; and
   means for producing a model based upon the construction alteration.

6. The apparatus according to claim 5, wherein said construction alteration includes a telescopic structure including at least one releasable part fitted on at least one support member.

7. The apparatus according to claim 5, wherein the construction alteration includes at least one occlusion rim.

8. The apparatus according to claim 5, wherein the construction alteration includes at least one tooth, tooth support member, part of a tooth, or tooth replacement and a relationship with an adjacent tooth.

9. The apparatus according to claim 5, wherein the construction alteration is effected by at least one macro model stored in the computer memory.

10. The apparatus according to claim 5, wherein the construction alteration is effected by at least one macro instruction carried out by the computer, wherein the macro instruction codes for mathematics and rules for creating the construction alteration.

11. The apparatus according to claim 1, wherein said construction includes a telescopic structure including at least one releasable part fitted on at least one support member.

12. The apparatus according to claim 11, wherein said telescopic structure is a cone construction.

13. The apparatus according to claim 11, wherein the releasable parts are joined together.

14. The apparatus according to claim 11, wherein the at least one support member is selected from the group consisting of an implant, a tooth, a part of a tooth, a tooth replacement, a support member for a tooth replacement, and a member anchored on an implant, a tooth, a part of a tooth, a tooth replacement, a support member for a tooth replacement.

15. The apparatus according to claim 11, wherein the releasable part is held in place on the support member by frictional forces.

16. The apparatus according to claim 1, wherein the construction includes at least one occlusion rim.

17. The apparatus according to claim 1, wherein the construction includes at least one tooth, tooth support member, part of a tooth, or tooth replacement and a relationship with an adjacent tooth.

18. The apparatus according to claim 1, wherein said at least one macro instruction represents a portion of at least one macro model stored in the computer memory.

19. The apparatus according to claim 1, wherein the construction is effected by at least one macro instruction carried out by the computer, wherein the macro instruction codes for mathematics and rules for creating the construction.

20. The apparatus according to claim 1, further comprising:

a stereocamera for reading the information input into the computer memory from information about the outer surface of a tooth, part of a tooth, tooth replacement, support member for a tooth replacement, or model or photograph thereof.

21. The apparatus according to claim 1, wherein the model is produced from a construction alteration and includes addition of material to an outer surface of a tooth or tooth replacement that prior to the addition of material was subjected to forces acting at right angles to a longitudinal axis of the tooth or tooth replacement, wherein the forces resulted from interaction of the outer surface of the tooth or tooth replacement with the outer surface of another tooth or tooth replacement, and wherein after the addition of material is subjected to forces from the outer surface of other tooth or tooth replacement substantially along the longitudinal axis.

* * * * *